United States Patent [19]
Tanhehco et al.

[11] Patent Number: 5,848,993
[45] Date of Patent: Dec. 15, 1998

[54] BULB SYRINGE PROVIDING FOR VISUAL OBSERVATION OF CONTENTS THEREOF AND FOR ENHANCED DEFLATION/INFLATION CONTROL

[75] Inventors: Benito Li Tanhehco; Steven Edward Saad, both of Powell; Brian Jay Donahue; Brian Jay Mitchell, both of Knoxville, all of Tenn.

[73] Assignee: DeRoyal Industries, Inc., Powell, Tenn.

[21] Appl. No.: 906,646

[22] Filed: Aug. 7, 1997

[51] Int. Cl.⁶ .................................................. A61M 5/00
[52] U.S. Cl. ........................ 604/217; 604/223; 604/227
[58] Field of Search .................................. 604/217, 216, 604/215, 214, 212, 187, 227

[56] References Cited

U.S. PATENT DOCUMENTS

| | | | |
|---|---|---|---|
| 1,961,489 | 6/1934 | Hein | 604/214 |
| 2,744,527 | 5/1956 | Barrett et al. | 604/215 X |
| 3,387,610 | 6/1968 | Richmond | 604/216 |
| 3,512,524 | 5/1970 | Drewe | 604/216 X |
| 3,938,514 | 2/1976 | Boucher | 604/216 X |

*Primary Examiner*—John D. Yasko
*Attorney, Agent, or Firm*—Paul E. Hodges

[57] ABSTRACT

A bulb syringe providing for uniform, hence repeatable, deflation/inflation of the bulb and a tactile-discernible limit of deflation of the bulb and resultant control over the consistency of degree of suction produced with the deflated bulb is allowed to inflate in response to its resiliency and memory. The bulb syringe includes a bottom portion having a spout and a top portion whose resiliency is enhanced by a plurality of ribs. The top and bottom portions are provided with equatorial shoulders which are joined and which establish a tactile-discernible limit of deflation of the top portion. In one embodiment, the bottom portion is provided with a pair of lugs on the outer surface therefor for receipt of the palmar surfaces of two adjacent fingers of a user. Preferably, the syringe is transparent or at least sufficiently translucent as permits the visual inspection of any fluid contained therein.

8 Claims, 3 Drawing Sheets

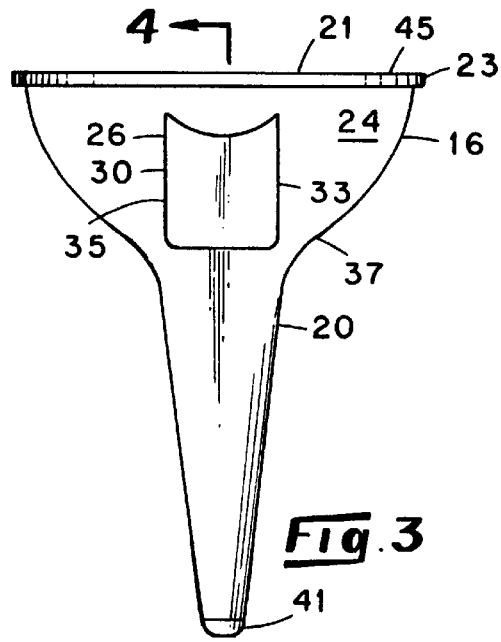
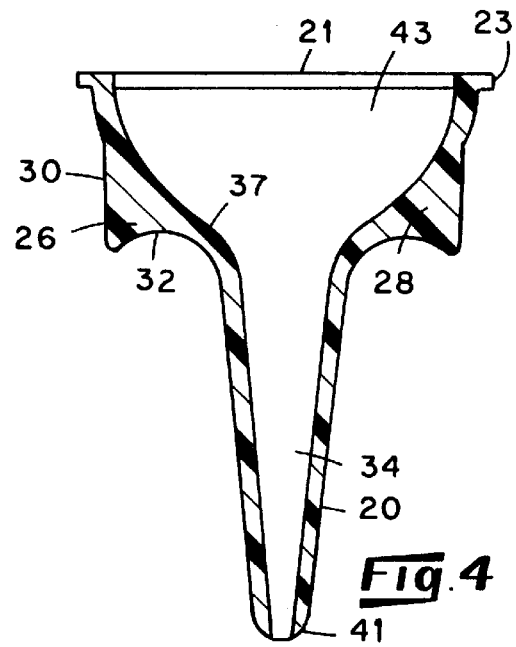
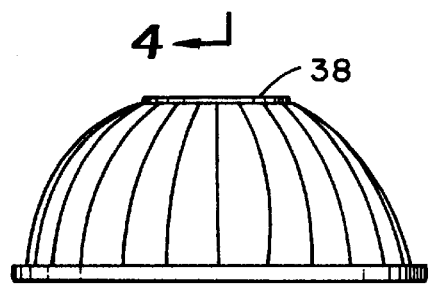
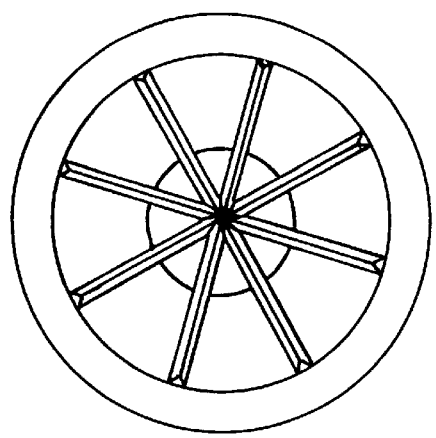
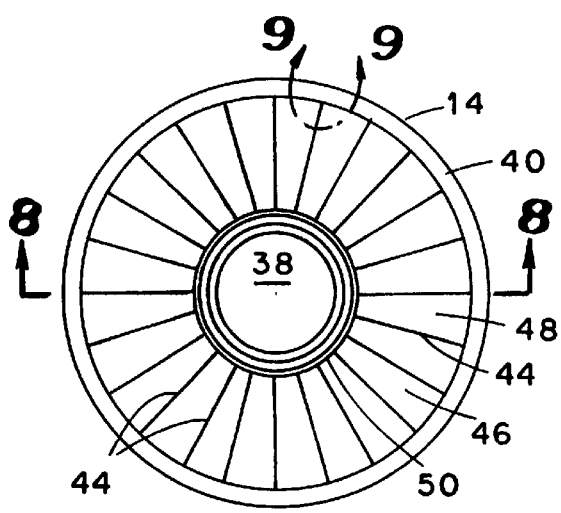
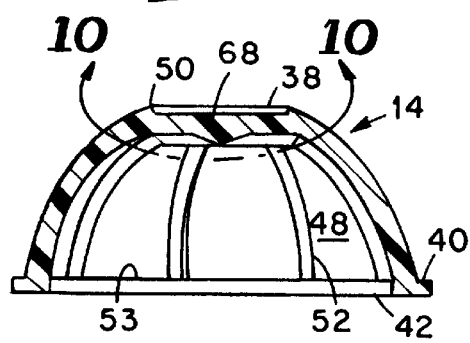

BULB SYRINGE PROVIDING FOR VISUAL OBSERVATION OF CONTENTS THEREOF AND FOR ENHANCED DEFLATION/INFLATION CONTROL

FIELD OF INVENTION

This invention relates to bulb syringes, particularly syringes designed and intended withdrawal of nasal fluids and/or for irrigation and like activities relating to infants.

BACKGROUND OF INVENTION

It is common practice in the medical field to employ a bulb syringe to withdraw nasal fluids from infants, and for irrigation and other purposes, particularly with infants. The number of these syringes sold annually for these purposes is very large. Present medical practice is to instruct new mothers in the use of a bulb syringe and to provide a bulb syringe for the mother to take home with her when she and her new baby leave the hospital. Pediatricians also commonly advise parents to use a bulb syringe to assist in keeping a baby or child's nasal passages clear of fluids.

The known bulb syringes of the type referred to above become very slippery and difficult to hold in the hand when the exterior surface of the bulb becomes wet. This lack of control over the bulb may prevent, or at least makes more difficult, the task of deflating the bulb by a measured amount to avoid injury to the child by reason of excessive suction being applied within the nasal cavity. Some prior art bulbs have been provided on their exterior surface with circumferential lands or shoulders or the like in an attempt to provide a more positive gripping surface on the bulb. This type treatment of the bulb surface is both generally ineffective in providing enhanced gripping of the bulb, and provides no measure of control over the extent of deflation of the bulb. No known bulb syringe provides a tactile-discrenible limit of deflation of the bulb, such that the parent can effectively control the degree of suction to which the child's nasal passage is subjected during withdrawal of nasal fluids. In one aspect of the prior art, bulb syringes commonly are provided in sizes, such as two-ounce and three-ounce capacities. This practice is further indicative of the need for a single bulb syringe which can be used to extract controlled amounts of nasal fluids.

Further, to the knowledge of the present inventor, at least the bulb portion of all bulb syringes presently in the marketplace are opaque. Accordingly, it is not possible to visually observe the contents of the bulb. In those instances where the bulb is used to withdraw nasal fluids it is especially important that the parent be able to determine whether there is blood and blood residue contained within the withdrawn nasal fluids, inasmuch as the presence of blood or blood residue can be indicative of problems not associated with the commonly discharged nasal fluids. Failure to detect such problems can result in failure of the parent to recognize that the child needs medical attention.

In spite of this strong and long-standing need, there is no known bulb syringe in the marketplace in which at least the bulb portion of the syringe is transparent or at least sufficiently translucent to permit the visual examination of the contents of the bulb and/or of the entire syringe. It is suggested that one reason for the failure of the art to provide a transparent or translucent bulb syringe relates to the fact that proper functioning of a bulb syringe requires very substantial resiliency and memory in the material of construction of the bulb, and prior to the present invention, these two somewhat competing requirements have not been met by those materials of construction for bulbs which are sufficient inexpensive to permit the fabrication of bulb syringes at reasonable cost to consumers.

SUMMARY OF INVENTION

In accordance with one aspect of the present invention, the present inventor provides a bulb syringe which provides for uniform, hence repeatable, deflation of the bulb and a tactile-discernible limit of deflation of the bulb, hence control over the consistency of the degree of suction produced when the deflated bulb is allowed to inflate in response to its resiliency and memory. This control over the extent of deflation of the bulb is provided, in one embodiment, by dividing the bulb into two hollow, hemispherical portions, referred to herein as the top and bottom portions of the bulb, by a circumferential shoulder that provides a definite limiting resistance, substantially in the nature of a barrier, to deflation of the bulb. The top portion of the bulb is provided with a uniform wall thickness and a series of specially designed ribs disposed on the interior and exterior surfaces of only the top portion of the bulb that establish and enhance the control over the deflation of the bulb. In a preferred embodiment, the bottom portion of the bulb is provided with a pair of lugs which project outwardly from the outer surface of the bottom portion of the bulb. These lugs are designed such that they rigidify the wall of the bottom portion of the bulb to render such wall resistant to collapse as the top portion of the bulb is collapsed in the bulb deflation process. These lugs, which preferably are spaced 180 degrees apart about the circumference of the wall of the bottom portion of the bulb, are further designed to provide finger grips of a type which enhance the ease with which the bulb may be grasped and held steady during use, including enhancement of the ability of the user to prevent rotation of the bulb in the user's hand during use and thereby effect the desired deflation of the bulb.

In accordance with another aspect of the present invention, the bulb is fabricated from a transparent or translucent material so that the contents of the bulb are visually observable. In one embodiment, the bulb is opaque or translucent and is provided with a transparent window which extends from the spout toward the apex of the bulb to provide a means for observing the contents of the bulb.

It is therefore an object of the present invention to provide an improved bulb syringe having enhanced deflation control, hence enhanced control of over the degree of vacuum produced by the syringe.

It is another object of the present invention to provide a bulb syringe which provides for the visual observation of the contents thereof.

It is another object of the present invention to provide a bulb syringe which is readily and securely grasped by the fingers of a user.

BRIEF DESCRIPTION OF FIGURES

FIG. 3 is a side elevational view of the bottom portion of a bulb syringe embodying various of the features of the present invention;

FIG. 4 is a sectional view, taken generally along line 4—4, of the bottom portion depicted in FIG. 3;

FIG. 5 is a side elevational view of the top portion of a bulb syringe embodying various of the features of the present invention;

FIG. 6 is a top plan view of the top portion of a bulb syringe as depicted in FIG. 5;

FIG. 7 is a bottom plan view of the top portion of a bulb syringe as depicted in FIG. 5;

FIG. 8 is a side elevational view, in section, of the top portion of a bulb syringe as depicted in FIG. 6, and taken generally along line 8—8 of FIG. 6;

DETAILED DESCRIPTION OF INVENTION

Figure 1:
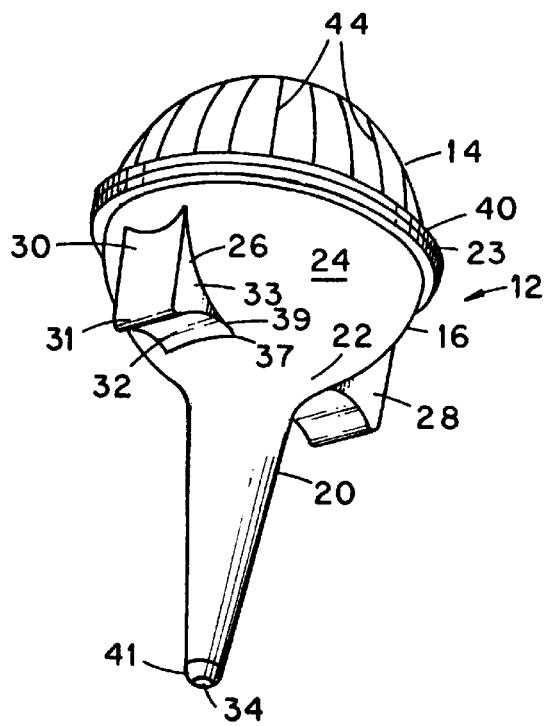
FIG. 1 is a perspective view of a bulb syringe embodying various of the features of the present invention.
Figure 2:
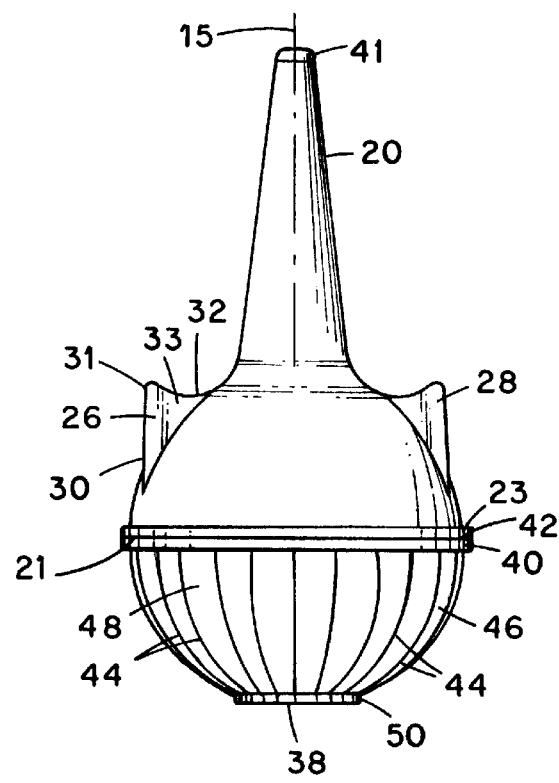
FIG. 2 is a side elevational view of the bulb syringe depicted in FIG. 1.
Figure 10:
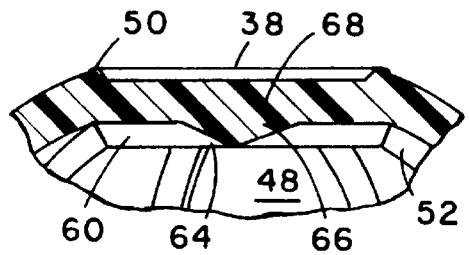
FIG. 10 is an enlarged detailed view of a portion of the top portion of a bulb syringe as depicted in FIG. 8 and taken generally along the line 10—10 of FIG. 8.
Figure 9:
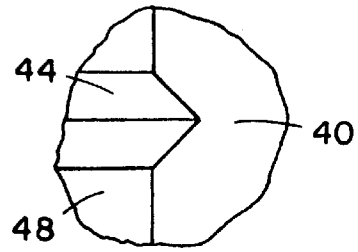
FIG. 9 is a detailed view, in section, of a portion of the bulb syringe depicted in FIG. 8, and taken generally along the line 9—9 of FIG. 8.
Figure 11:
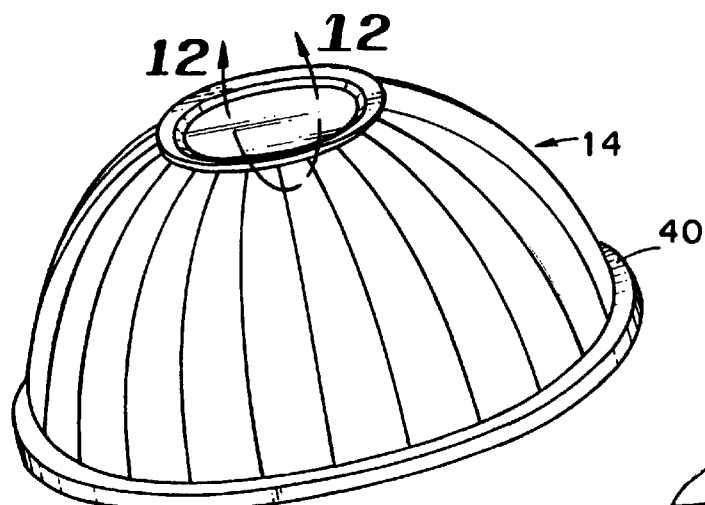
FIG. 11 is a perspective view of a top portion of a bulb syringe and depicting various of the features of the present invention.
Figure 12:
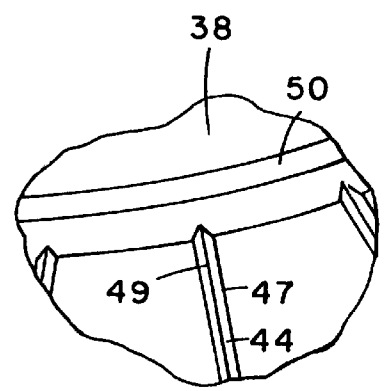
FIG. 12 is a fragmented view of a portion of the bulb syringe as depicted in FIG. 11 and taken generally along the line 12—12 of FIG. 11.
Figure 13:
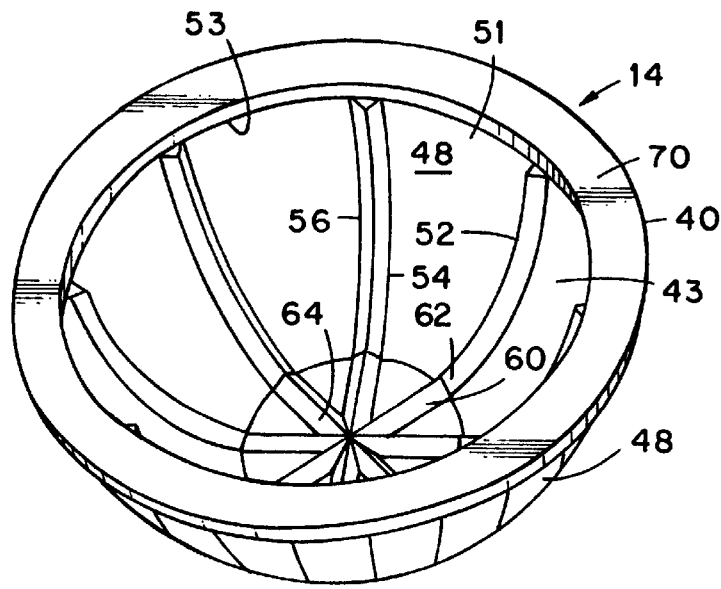
FIG. 13 is a perspective view of the interior of a top portion of a bulb syringe as depicted in FIG. 11.

With reference to the several figures, particularly FIGS. 1 and 2, one embodiment of a bulb syringe 12 in accordance with the present invention is depicted and includes a top portion 14 and a bottom portion 16 and having a longitudinal centerline 15. The bottom portion 16 is generally hollow and hemispherical in geometry and includes a circular wall 24 that extends between the equator 21 and the apex 22 of the bottom portion. A funnel spout 20 is attached to the wall 24 at the apex 22 of the bottom portion. The funnel spout 20 is provided with an internal passageway 34 leading from exteriorly of the bulb syringe into the hollow interior thereof. At the equator 21 of the bottom portion, there is provided a circumferential shoulder 23. The circular wall 24 of the bottom portion has integrally formed therewith first and second reinforcement members 26 and 28. These members are spaced apart from one another about the circumference of the wall 24 by 180 degrees and each includes a planar first face 30 and a concave second face 32.

The top portion 14 of the depicted bulb syringe is likewise generally hollow and hemispherical in geometry. It includes a flat circular apex 38 and a circumferential shoulder 40 disposed about the equator 42 thereof. A plurality of elongated ribs 44 are integrally formed on the outer surface 46 of the circular wall 48 of the top portion, and extend from the rim 50 of the circular apex 38 along the outer wall of the top portion to terminate adjacent the shoulder 40. These ribs are spaced apart equal distances about the circumference of the outer wall 48. Each preferably is of a triangular cross section, with the base of the triangle being adjacent the outer wall and the apex being distal to the outer wall.

The top and bottom portion are joined one to another at their respective shoulders to define an air-tight bulb.

More specifically, in a preferred embodiment, the bottom portion 16 of the present bulb syringe 12 serves relative passive functions, namely as a reservoir for liquids that are drawn into the bulb, as a noncollapsible support for the collapsible top portion 14 of the bulb, as a support for the funnel spout 20, and as a location for grasping of the bulb during use thereof. To this end, the circular wall 24 of the bottom portion is reinforced by at least first and second lugs 26 and 28. In the preferred embodiment, these lugs are integrally formed with the wall 24. The depicted lugs preferably are identical. The lug 26 includes a first outer planar wall 30 that is oriented substantially parallel to, and laterally spaced apart from, the longitudinal centerline 15 of the syringe, a second outer concave wall 32 that extends between the terminal end 31 of the first wall 30 and the wall 24, and is oriented generally normal to the longitudinal centerline 15 of the syringe. This second wall 32 presents an arcuate, i.e. concave, surface which is adapted to receive therein a finger of a user of the syringe such that the user's finger will be spaced laterally of the longitudinal centerline of the syringe and generally in a plane that is normal to the longitudinal centerline. The arcuate geometry of this wall effectively defines a cradle within which the finger is received so that the finger is readily and securely engaged with the bottom portion of the bulb. This lug 26, further includes opposite planar side walls 33 and 35. In the preferred embodiment, the lug 26 is solid (see FIG. 4) and is formed simultaneously with the formation of the bottom portion 16. The second lug 28 is located 180 degrees around the circumference of the wall 24 from the first lug 26 and, as noted, preferably is identical to the first lug. This second lug 28 serves to receive and cradle therein a further finger of the user of the syringe such that the user can securely grasp the bottom portion of the bulb between two adjacent fingers of one hand. When so grasped, the funnel spout 20 is disposed between the two fingers of the user so that the user's fingers are in position to both support the bulb in a direction parallel to its longitudinal centerline and to squeeze the funnel spout to maintain the engagement of the fingers with the cradling surfaces of the first and second lugs. By this means, the user can exert enhanced "one-hand" control over the position of the funnel spout during use of the syringe, a distinct advantage when treating a small child.

Aside from their function as grasping and positioning aids, the first and second lungs further function to reinforce the wall 24 against collapse thereof. To this end, the lugs 26 and 28 are of a width equal to about one-sixth of the circumference of the wall 24 as measured at the junction 37 of the inner edge 39 of the concave wall 32 with the wall 24 of the bulb. Further, each lug extends over a distance of about four-fifths of the arcuate distance between the junction 37 of the funnel spout 20 with the wall 24 and the shoulder 23 of the wall 24. The lugs 26 and 28, in combination, therefore, occupy an area of about one-third of the total area of the wall 24. Importantly, the only engagement of the user's fingers with the bottom portion of the bulb which is effective in the deflation of the bulb, is engagement with the concave walls of the lugs 26 and 28. As will appear more fully hereinafter, notably, this engagement causes the deflation forces exerted against the top portion 14 of the bulb to be counteracted by the user's fingers only through the lugs 26 and 28 and in a direction substantially parallel to the deflation forces. The lugs, therefore, assume substantially all of the deflation forces so that the wall 24 of the bottom portion of the bulb does not collapse during deflation of the bulb. Among other things, this allows the wall 24 of the bottom portion of the bulb to be fabricated from a more wide range of materials of construction, ultimately resulting in less cost of fabrication thereof.

As seen in FIG. 4, the funnel spout 20 of the present bulb syringe is tapered inwardly from a maximum diameter at its junction 37 with the apex 22 (FIG. 1) of the bottom portion of the bulb toward its distal end 41 in the manner well known in the art. The spout 20 defines an open passageway 34 along its length, this passageway being in fluid communication with the interior 43 of the bulb.

At the equator 21 of the bottom portion of the bulb there is provided a circumferential shoulder 23. This shoulder includes a flat outer surface 45 which is designed to mate with, and be joined to the equatorial shoulder 40 of the top portion of the bulb. The shoulder 23 projects outwardly from the equatorial circumference of the bottom portion of the bulb and is of generally a rectangular cross-section. This geometry of the shoulder tends to oppose circumferential expansion of the shoulder as will be noted further hereinafter.

With particular reference to FIGS. 6–13, in the depicted embodiment, the top portion 14 of the bulb syringe is hollow and hemispherical in geometry. This top portion is defined by a circular wall 48 that extends from a planar apex 38 to an equatorial shoulder 40. This wall 48 is fabricated of a resilient material, preferably a material which exhibits excellent memory to return to its original hemispherical geometry after having been deformed from such geometry and the deformation forces have been released. As will appear further herein, the return of the top portion 14 of the bulb is not solely dependent upon the inherent memory of the material of construction of the top portion, but rather specific design features are provided to enhance this property of the top portion. Notably, the bottom portion of the bulb syringe is not provided with such design features.

The outer surface 46 of the wall 48 is provided with a plurality of radially oriented, spaced apart, ribs 44. Each rib, in a preferred embodiment is of a triangular cross-section, (see FIG. 13) including a base 47 and an apex 49, the base being disposed adjacent the outer surface 46 of the wall 48 with the apex of the rib projecting outwardly from the wall 48. Each rib preferably is integrally formed with the wall 48 so that the rib is deformed as the wall 48 is deformed. In one embodiment, there are 24 ribs equally spaced apart by 15 degrees about the circumference of the top portion 14. Each rib extends between the rim 50 of the apex 38 of the top portion, radially along the circular wall 48 to the shoulder 40.

The interior surface 51 of the wall 48 of the top portion is similarly provided with a plurality of ribs 52 that preferably are integrally formed with the wall 48. Each rib preferably is of a triangular cross-section, with the base 54 thereof being disposed adjacent the wall 48 and the apex 56 thereof projecting outwardly from the wall and interiorly of the hollow hemispherical top portion. In the preferred embodiment, each rib extends radially from a location on an imaginary circle that is concentric with the rim 50 of the circular apex 38, but located interiorly of the top portion, to a location on the interior wall 53 of the equatorial shoulder 40 of the top portion. As with the ribs 44, the ribs 52 move in response to deformation of the wall 48. The ribs 52, however, are chosen to be substantially, e.g. about twice the size (i.e. wall dimensions) of the ribs 44 so that the ribs 52 require a greater force to deform them than do the ribs 44. Further, the ribs 52 exert a greater force tending to urge the wall 48 toward its relaxed hemispherical geometry when any deformation forces have been released from the top portion, than do the ribs 44.

Interiorly of the top portion, the planar apex 38 of the top portion is provided with a plurality of modified ribs 60 which originate at the center of the apex 38 and extend radially therefrom to join the apical ends 62 of the ribs 52. One such modified rib 60 is provided for each of the ribs 52. With specific reference to FIG. 9, each of the ribs 60 includes a tapered end 64 adjacent the center of the apex 38. The center of the apex is provided with a conical projection 66 that projects inwardly of the top portion and preferably is integrally formed with the tapered ends of the ribs 60 so as to become a part thereof. The confluence of the tapered ends 64 of the ribs 60 and the conical projection 66 provide a relatively yieldable central portion 68 of the apex 38. This yieldable portion 68 of the apex 38, in combination with the rim 50 and the ribs 60, has been found useful in providing tactile identification of the apex by the user of the syringe, such identification being highly desirable to provide a "starting point" location for the application of the user of a deflation force to the top portion as will appear more fully hereinafter.

At the equator 42 of the top portion 14 there is provided a circumferential shoulder 40 having a outer flat face 70 which is designed to mate with, and be joined to the face 45 equatorial shoulder 23 of the bottom portion of the bulb. The shoulder 40 projects outwardly from the equatorial circumference of the top portion of the bulb and is of generally a rectangular cross-section. Like the shoulder 23 of the bottom portion, this geometry of the shoulder 40 of the top portion tends to oppose circumferential expansion of the shoulder. The use of two shoulders in joining of the top and bottom portions of the bulb is useful in assembly of the bulb, but also importantly, when the two shoulders are joined at their outer faces, they complement each other with respect to the resistance which they exert to circumferential expansion of the equator of the bulb.

The top and bottom portions of the bulb syringe of the present invention preferably are fabricated from a transparent or at least translucent material to provide for visual observation and examination of the contents of the bulb. One suitable material is polyvinylchloride (PVC). Other materials of construction may be employed, however, if it is not required or desired that the contents of the bulb be visually observable. Such materials may include latex, natural rubber, resilient polymers, and others. In any event, the material of construction of at least the top portion of the bulb must be resilient and have sufficient memory as will cause the top portion to return to its relaxed hemispherical geometry following release of any deformation forces exerted thereto. PVC having a Rockwell durometer of between about 45 and 75 fabricated into a wall 48 for the top portion of the bulb having a wall thickness of about 0.12 inch thickness, has been found satisfactory for the present invention. Preferably, this PVC has a Rockwell durometer of between about 55 and 65. In the embodiment where the bottom portion 16 includes the lugs 26 and 28, or their equivalent, the bottom portion may be fabricated from the same material as is the top portion 14. The ribs 44 and 52, being integrally formed with the wall of the top portion, exhibit an inherent resiliency and memory which is characteristic of the material of construction of the wall. As noted, however, the cross sectional geometries of the ribs enhance their contribution to the overall resiliency and memory of the top portion 14.

Joining of the equatorial shoulders of the top and bottom portions of the bulb may be accomplished by various means known in the art. Thermoplastics, such as PVC, are expeditiously joined in fluid-tight relationship by radio-frequency heat sealing techniques well known in the art.

Figure 15:
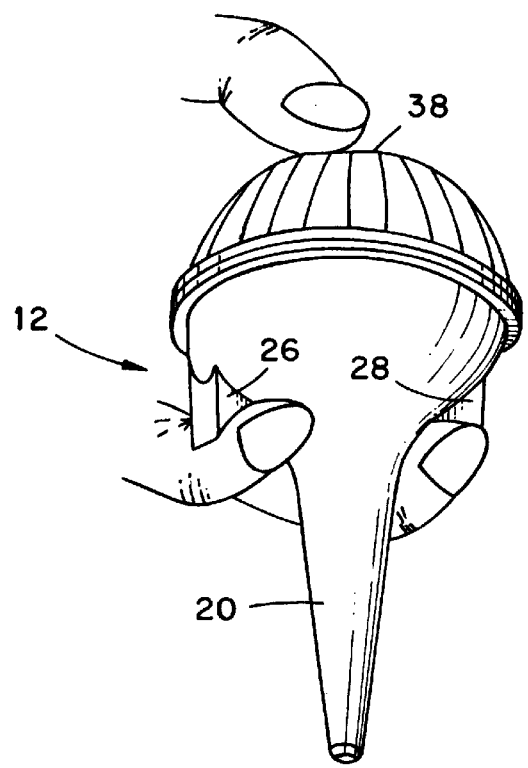
FIG. 15 is a perspective view of a bulb syringe of the present invention as grasped in the fingers of a user.

As depicted in FIG. 15, in use, the bulb syringe is grasped between adjacent fingers of the user's hand with the fingers lying alongside opposite sides of the funnel spout and with the palmer surfaces of the fingers residing in the concave walls of the lugs 26 and 28. This grasping of the bulb positions the user's thumb adjacent the apex 38 of the top portion of the bulb in ready position to exert a deflation force against the apex 38 in a direction substantially parallel to the longitudinal centerline of the bulb, which is also inline with the funnel spout 20. Initially, upon the user's thumb contacting the apex 38, the user tactilely recognizes the center of the apex, using the rim 50 as a reference. Thereafter, upon the application of a relatively slight pressure against the apex 38, by reason of the construction of the modified ribs 60 including their joinder with the projection 66 on the interior of the apex, the user further tactilely recognizes that the center of the apex yields preferentially, again ensuring the user that the deflation pressure is being applied parallel to and in line with the longitudinal centerline of the bulb. Maintenance of this alignment of the applied deflation pressure to the top portion of the bulb ensures that the deflation pressure is uniformly distributed about the circular wall 48 of the top portion of the bulb. As this uniformity distributed deflation pressure is increased to deform the wall 48 of the top portion and move the apex 38 inwardly of the hollow bulb, the user experiences a uniform increase in resistance to deflation of the top portion of the bulb until the apex approaches the equatorial plane of the joinder of the equatorial shoulders of the top and bottom portions of the bulb. In accordance with one aspect of the present invention, when the apex 38 has been moved to, slightly past, the common equatorial plane of the joined shoulders, there is developed a sharp increase in resistance to further deflation of the top portion of the bulb by reason of the resistance to circumferential expansion provided by the joined shoulders 23 and 40 and by the combined deformation resistance of the ribs 44 and 52 of the top portion 14 as their respective angles of bending become more acute. This increase in resistance to further deformation of the top portion of the bulb is experienced by the user, thereby signaling the achievement of a level of deflation of the bulb, hence a recognition that if the deflation forces are removed by the user, the top portion of the bulb will return to its relaxed hemispherical geometry and thereby establish a given degree of vacuum (suction) at the entrance to the passageway 34 in the distal end of the funnel spout.

Notably, the aforedescribed applied force-resistance relationship is attainable when the applied force effects uniform deformation of the wall 48. As noted, this situation maximally exits when the deflation force is applied parallel to and inline with the longitudinal centerline of the bulb syringe. Under these conditions, the ribs 44 and 52 on the wall 48 of the top portion uniformity collapse as the wall is deformed. Importantly, these ribs and the wall 48 of the top portion also uniformly return to their relaxed state upon release of the deformation forces, thereby developing a uniform suction at the entrance to the passageway 34 of the funnel spout as the top portion returns to its relaxed state. This factor, in combination with the tactile recognition by the user of achievement of a given level of deflation of the top portion, provides the user with confidence that the suction exerted by the syringe is of a value that is proper for the treatment desired, and that the suction is maximally and uniformly exerted.

Figure 14:
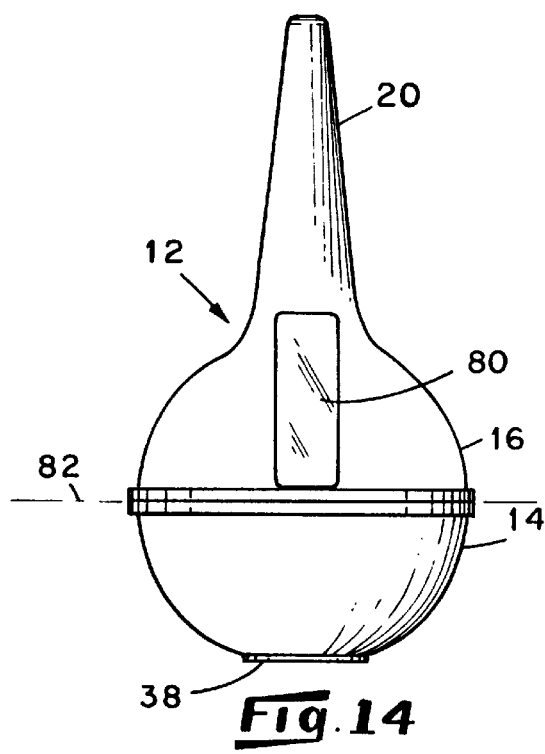
FIG. 14 is a side elevational view of one embodiment of a bulb syringe having a transparent window through which the contents of the bulb may be visually observed.

As noted, fluids drawn into the bulb are visually observable when the material of construction of the bulb is transparent, or at least translucent, as is the case with polyvinylchoride. In an alternative embodiment as depicted in FIG. 14, the material of construction of the bulb may be opaque or translucent and provided with a window 80 which extends from the spout 20 toward the apex of the bulb to provide a means for visual observation of fluid, if any, within the bulb. The depicted window extends from the spout to the transverse centerline 82 of the bulb, but the window may extend into the top hemispherical portion of the bulb as desired. The width of the window may be of any desired width so long as there is provided ample opportunity for a user to readily observe the contents, if any, of the bulb, including the level of such contents, if any. The window may be formed in any of several ways, but in one embodiment, the window may be formed of a transparent material and bonded about its periphery to the side edges of an opening provided in the wall of the bulb.

Whereas the present invention has been described in specific detail, it is intended that the invention be limited only as set forth in the claims attached hereto. For example, whereas the top and bottom portions of the present bulb are described and depicted herein as being hemispherical, and whereas hemispherical geometries of the top and bottom portions are preferred, it is to be recognized that the geometry of the top and bottom portions, particularly the bottom portion, could be other than precisely hemispherical. In this respect, a major requirement for these top and bottom portions is that they possess substantially identical or at least equivalent equatorial shoulders that are joinable.

What is claimed:

1. A bulb syringe for use in medical applications comprising
   a resilient portion having a wall defining a hollow bulbous geometry thereof,
   spout means secured to said resilient portion for providing inhalation of fluid from a source external to the syringe and exhalation of fluid out of the syringe in response to inflation and deflation of said resilient portion,
   at least a portion of said wall of said resilient portion being sufficiently transparent or translucent as permits the visual observation of the presence of fluid within said resilient portion,
   said resilient portion including a longitudinal centerline and first and second lugs disposed opposite one another on said wall of said resilient portion and projecting outwardly from said wall to present first and second concave surfaces that are oriented substantially normal to the longitudinal centerline of said resilient portion and adjacent said spout whereby the syringe may be grasped between two adjacent fingers of the user with the palmer surfaces of the user's fingers residing in said concave surfaces and with the fingers on opposite sides of said spout.

2. The bulb syringe of claim 1 wherein the combined area of said wall of said resilient portion occupied by said first and second lugs is sufficient to substantially rigidify said wall.

3. A bulb syringe having a tactile-discernable limit of deflation comprising
   a hollow bottom portion including a circular wall having an equatorial shoulder, an apex and a longitudinal centerline passing through the center of said equatorial shoulder and said apex,
   a spout leading from said apex of said bottom portion and including means defining a fluid passageway from a location exterior to said bulb syringe through said spout to the interior of said bulb syringe,
   a hollow generally hemispherical top portion including a resilient circular wall having inner and outer surfaces, an equatorial shoulder, a substantially planar apex and a longitudinal centerline passing through the center of said equatorial shoulder and said apex, a first plurality of circumferentially spaced apart resilient ribs formed integrally with said wall of said top portion and projecting outwardly from said outer surface of said wall, individual ones of said ribs extending between said apex and said equatorial shoulder, a second plurality of resilient ribs formed integrally with said wall, projecting inwardly from said inner surface of said wall, and being substantially equally spaced apart circumferentially of said wall of said top portion, individual ones of said second plurality of ribs being substantially more resistive to flexing thereof than individual ones of said first plurality of ribs and extending from proximate said apex to said shoulder, said ribs providing enhanced circumferentially-equal resistance to movement of said apex toward said equatorial shoulder, said resistance achieving a maximum as said apex approaches and moves past said equatorial shoulder, said bottom and top portions being joined in fluid-tight relationship at their respective equatorial shoulders and with their respective longitudinal centerlines aligned, said joined shoulders producing a resistive barrier to movement of said apex of said top portion therepast and thereby developing a tactile-discernable limit of deflation of said top portion.

4. The bulb syringe of claim 3 and including a third plurality of resilient ribs formed integrally with said apex of said top portion and projecting inwardly of said top portion, said plurality of ribs radiating outwardly from the longitudinal centerline of said top portion and having tapered ends adjacent said longitudinal centerline, said ribs being more readily flexed in response to application of deformation force thereto at, and inline with, the longitudinal centerline of said top portion, than at other locations distant from, and/or at an angle to, the longitudinal centerline of said top portion, thereby providing a tactile indication of the alignment of a deformation force being applied to said top portion.

5. The bulb syringe of claim 3 and including first and second lugs disposed opposite one another on said wall of said bottom portion and projecting outwardly from said wall to present first and second concave surfaces that are oriented substantially normal to the longitudinal centerline of said bottom portion and adjacent said spout whereby said bulb syringe may be grasped between two adjacent fingers of a user with the palmar surfaces of the user's fingers residing in said concave surfaces and with the fingers on opposite sides of said spout.

6. The bulb syringe of claim 5 wherein the combined area of said wall of said bottom portion occupied by said first and second lugs is sufficient to substantially rigidify said bottom wall relative to the rigidity of said wall of said top portion.

7. The bulb syringe of claim 5 wherein each of said first second lugs includes first and second planar walls, each of said walls being oriented spaced apart from, and substantially parallel to the longitudinal centerline of said bottom portion.

8. The bulb syringe of claim 3 wherein the material of construction of at least said bottom portion is at least sufficiently translucent to permit visual inspection of any fluid contents within said bottom portion.

* * * * *